US006274775B1

(12) United States Patent
Giera et al.

(10) Patent No.: US 6,274,775 B1
(45) Date of Patent: Aug. 14, 2001

(54) PROCESS FOR THE PREPARATION OF NITROSOBENZENES

(75) Inventors: Henry Giera, Grosskitzighofen; Michaela Meiers, Speyer; Uwe Hugger, Rellingen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/707,261

(22) Filed: Nov. 6, 2000

(30) Foreign Application Priority Data

Nov. 12, 1999  (DE) .............................................. 199 54 397

(51) Int. Cl.[7] .................................................. C07C 205/06

(52) U.S. Cl. .......................... 568/584; 568/587; 568/939; 568/940

(58) Field of Search ................................... 568/584, 587, 568/939, 940

(56) References Cited

FOREIGN PATENT DOCUMENTS

| 1680689 | 9/1991 | (RU) . |
| 2042661 | 8/1995 | (RU) . |
| 2044724 | 9/1995 | (RU) . |
| 2090542 | 9/1997 | (RU) . |

OTHER PUBLICATIONS

Journal of Organic Chemistry, vol. 58, No. 14, Jul. 2, 1993, pp. 3633–3638, Sigeki Sakaue et al, "Oxidation of Aromatic Amines with Hydrogen Peroxide Catalyzed by Cetylpyridinium Heteropolyoxometalates".

J. Chem. Soc., Chem. Commun. (month unavailable) 1993, pp. 1510–1511, Stefano Tollari et al, "Catalytic Oxidation of Primary Aromatic Amines to the Corresponding Nitroso Compounds by $H_2O_2$ and $[Mo(O)(O_2)_2(H_2O)(hmpa)]$ (hmpa=Hexamethylphosphoric Triamide)".

Russian Journal Organic Chemistry, vol. 31, No. 12, (month unavailable) 1995, pp. 1640–1642, E. B. Mel'nikov et al, "Oxidation of Primary Aromatic Amines, Catalyzed by Tungsten Compounds*".

Journal of Organic Chemistry, vol. 60, No. 5, Mar. 10, 1995, pp. 1326–1331, Zuolin Zhu et al, "Kinetics and Mechanism of Oxidation of Anilines by Hydrogen Peroxide as Catalyzed by Methylrhenium Trioxide".

Analytische Chemie fur die Praxis, (month unavailable) 1982, pp. 37–41, "Kontroll–Methoden für Ergebnisse".

*Primary Examiner*—Johann Richter
*Assistant Examiner*—Brian J. Davis
(74) *Attorney, Agent, or Firm*—Joseph C. Gil; Noland J. Cheung

(57) ABSTRACT

The invention relates to a process for the preparation of nitrosobenzene from aromatic amines by oxidation with hydrogen peroxide in the presence of a catalyst based on compounds of tungsten and/or molybdenum without the addition of the organic solvents conventionally used.

3 Claims, No Drawings

PROCESS FOR THE PREPARATION OF NITROSOBENZENES

FIELD OF THE INVENTION

The invention relates to a process for the preparation of nitrosobenzenes from aromatic amines by oxidation with hydrogen peroxide in the presence of a catalyst without the addition of the organic solvents conventionally used.

BACKGROUND OF THE INVENTION

The preparation of nitrosobenzene, which is an important intermediate, is known and can be carried out by various methods. It can be used for the synthesis of antioxidants and stabilizers in the rubber and polymers industry, and in particular for the production of 4-aminodiphenylamine (4-ADPA)."

One method for the preparation of nitrosobenzenes is oxidation of corresponding aromatic amines with suitable oxidizing agents, such as hydrogen peroxide, in the presence of a catalyst and in the presence of a suitable solvent.

The preparation of nitrosobenzenes from aromatic amines by catalytic oxidation with hydrogen peroxide is described, for example, by S. Sakaue, T. Tsubakino, Y. Nishiyama, Y. Ishii. *Org. Chem.* 1993, 58, 3633; S. Tollari, M. Cuscela, F. Porta, *J. Chem. Soc., Chem. Commun.* 1993, 1510 and in RU-A 1680689; RU-A 2042661; RU-A 2044724; RU-A 2090542 and by E. B. Mel'nikov, G. A. Suboch, E. Yu Belyaev, *Russ. J. Org. Chem.* 1995, 31, 160–1642 and Z. Zhu, J. H. Espensen, *J. Org. Chem.* 1995, 60, 1326–1332.

Disadvantages of the processes mentioned are, for example, the use of high-risk solvents, such as chloroform, in amounts which are not practicable on a large industrial scale in order to achieve good yields, the use of toxic compounds, such as hexamethylphosphoric acid triamide, in the preparation of the catalyst, the use of additional co-catalysts and the use of relatively large amounts of catalyst, as well as the use of expensive catalysts. Because of the disadvantages mentioned, a process operated on a large industrial scale would be uneconomical, associated with extensive safety measures.

It has now been found that nitrosobenzenes can be prepared from aromatic amines by catalytic oxidation with hydrogen peroxides in an industrially simple manner and avoiding the disadvantages described above if the oxidation is carried out without the addition of solvent.

SUMMARY OF THE INVENTION

The present invention therefore provides a process for the preparation of nitrosobenzenes of the general formula

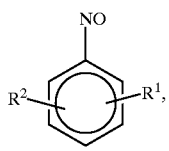

wherein
$R^1$ and $R^2$ are identical or different and represent hydrogen, $C_1$–$C_4$-alkyl or $C_1$–$C_4$-alkoxy,
by oxidation of corresponding aromatic amines, which is characterized in that the oxidation is carried out with hydrogen peroxide in the presence of an oxidation catalyst based on tungsten compounds and/or molybdenum compounds at temperatures of 5 to 25° C. in the absence of an organic solvent at a molar ratio of aromatic amines to hydrogen peroxide to oxidation catalyst of (1):(2.0 to 5.0):(0.001 to 0.05). Preferably aromatic amines, such as for example aniline, o-, m- and p-toluidine and o-, m- and p-anisidine, are used and particularly preferably aniline.

DETAILED DESCRIPTION OF THE INVENTION

Nitrosobenzenes of the above formula in which $R^1$ and $R^2$ represent hydrogen or methyl or methoxy groups are preferably prepared. The preparation of nitrosobenzene (i.e., $R^1$ and $R^2$=hydrogen) is especially preferred.

Therefore aniline, mono- and di-methyl- as well as mono- and di-methoxy-substituted anilines are preferred.

The process according to the present invention is preferably carried out at temperatures of 15 to 25° C.

The hydrogen peroxide employed according to the present invention is conventionally used in the aqueous form in a concentration of 15 to 80, preferably 30 to 50 wt. % hydrogen peroxide.

The process according to the invention is preferably carried out at a molar ratio of aromatic amines to hydrogen peroxide to oxidation catalyst of (1):(2.5 to 4.5):(0.003 to 0.02).

Possible oxidation catalysts to be employed according to the present invention are the oxidation catalysts, which are known from the appropriate literature and are based on tungsten compounds and molybdenum compounds. Molybdic acid and tungstic and molybdic and tungstic oxides, salts of molybdic and tungstic acids, salts of polymolybdic and polytungstic acids, molybdenum- and tungsten-containing polyoxometallates, molybdenum- and tungsten-containing heteropolyacids and salts thereof and molybdenum- and tungsten-oxo complexes are preferred.

Tungstatophosphoric acid, peroxocetylpyridinium molybdophosphate (PCMP) tetrakistetrabutylammonium octamolybdate, cetylpyridinium tungstatophosphate (CTP), cetylpyridinium molybdatophosphate (CMP), molybdenum dioxide bisacetylacetonate, sodium molybdate and/or sodium tungstate are especially preferred.

The catalysts can be employed either individually or as a mixture with one another. The most favorable mixing ratio can easily be determined by appropriate preliminary experiments and depends, inter alia, on the reaction conditions used.

Once nitrosobenzene have been prepared according to the invention, the resulting nitrosobenzene can be isolated from the reaction mixture in a conventional manner, e.g. by filtering off the solid, which has precipitated out, washing the solid with water and then drying it.

The nitrosobenzenes are obtained in yields of 50 to 95% of theory and in purities of ≧95%.

In contrast to the prior art to date, the process according to the present invention is particularly surprising that because it can be carried out without the addition of solvent. No loss in yield or in purity is experienced. Since the use of additional solvent can be omitted in the process according to the invention, the method is particularly economical.

EXAMPLES

General working instructions:

The catalyst is initially introduced into the reaction vessel, 100 μl (1.10 mmol) aniline are added and 350 μl (3.4 mmol) hydrogen peroxide are added. The reaction temperature is 20° C. After 2 hours, the reaction is terminated and the yield is determined by a GC method in accordance with 1.) Vogel's, Textbook of Quantitative Chemical Analysis, 5th Edition, Longwan Scientific & Technical, p. 247
2.) H. Hulpke, H. Hartkamp, G. Tölg (ed.), Analytische Chemie fuir die Praxis, K. Beyermann, Organische Spurenanalyse, G. Thieme Verlag, Stuttgart, New York, 1982, p. 37–41.

| Example no. | Catalyst | Amount of catalyst (eq) | Yield (%) |
|---|---|---|---|
| 1 | $H_3PW_{12}O_{40}$ | 0.003 | 51.0 |
| 2 | PCMP | 0.003 | 90.2 |
| 3 | $[(n-C_4H_9)_4N]_4[Mo_8O_{26}]$ | 0.004 | 94.4 |
| 4 | CTP | 0.003 | 61.0 |
| 5 | CMP | 0.003 | 90.8 |
| 6 | $MoO_2(acac)_2$ | 0.02 | 80.6 |
| 7 | $Na_2MoO_4 \cdot H_2O$ | 0.02 | 71.0 |

EXAMPLE 8

465 g (5 mol) aniline are added dropwise to a mixture of 22.5 g (0.068 mol) sodium tungstate and 1,457 g (12.9 mol) hydrogen peroxide at 20° C. The reaction mixture initially turns yellow-green in color and a beige solid precipitates out. After the addition of aniline, the solid is filtered off, washed several times with a total of 500 ml water and dried over calcium chloride. 485 g.(91% of theory) of a beige-brown solid with a content of 98% nitrosobenzene are obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of nitrosobenzenes of the general formula

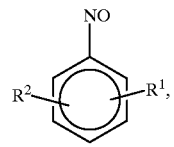

wherein $R^1$ and $R^2$ are identical or different and represent hydrogen, $C_1$–$C_4$-alkyl or $C_1$–$C_4$-alkoxy, comprising the step of oxidizing of corresponding aromatic amines, wherein the oxidation is carried out with hydrogen peroxide in the presence of an oxidation catalyst based on tungsten compounds, molybdenum compounds, and mixtures thereof at temperatures of 5 to 25° C. in the absence of an organic solvent at a molar ratio of aromatic amines to hydrogen peroxide to oxidation catalyst of(1):(2.0 to 5.0):(0.001 to 0.05).

2. A process for the preparation of nitrosobenzene according to claim 1, wherein said molar ratio of aromatic amines to hydrogen peroxide to oxidation catalyst is (1):(2.5 to 4.5):(0.003 to 0.02).

3. A process for the preparation of nitrosobenzene according to claim 1, wherein said oxidation catalyst is selected from the group consisting of molybdic acid and tungstic and molybdic and tungstic oxides, salts of molybdic and tungstic acid, salts of polymolybdic and polytungstic acids, molybdenum- and tungsten-containing polyoxometallates, molybdenum- and tungsten-containing heteropolyacids and salts thereof and molybdenum- and tungsten-oxo complexes.

* * * * *